United States Patent

Bertozzi

[11] 4,122,065
[45] Oct. 24, 1978

[54] TIN SALTS OF DIMERCAPTOETHYL FORMAL, RELATED COMPOUNDS AND PVC RESINS STABILIZED THEREWITH

[75] Inventor: Eugene R. Bertozzi, Yardley, Pa.

[73] Assignee: Thiokol Corporation, Newtown, Pa.

[21] Appl. No.: 863,754

[22] Filed: Dec. 23, 1977

[51] Int. Cl.² ............................ C07F 7/22; C08K 5/58
[52] U.S. Cl. ............................ 260/45.75 S; 260/429.7; 106/15 R; 424/288
[58] Field of Search ............ 260/45.75 S, 45.75 K, 260/429.7; 106/15 AF; 424/288

[56] References Cited

U.S. PATENT DOCUMENTS

| | | | |
|---|---|---|---|
| 2,752,325 | 6/1956 | Leistner et al. | 260/45.75 S |
| 3,242,201 | 3/1966 | Cramer et al. | 260/429.7 |
| 3,441,580 | 4/1969 | Katsumura et al. | 260/429.7 |
| 3,936,482 | 2/1976 | Sagi et al. | 260/429.7 |

*Primary Examiner*—V. P. Hoke
*Attorney, Agent, or Firm*—Stanley A. Marcus; Royal E. Bright

[57] ABSTRACT

Tin salts formed by the reaction between di-lower alkyl or diaryl tin oxides, and dimercaptoethyl formal and similar dimercapto compounds are disclosed. The final products are useful as ultraviolet light stabilizers for poly(vinyl chloride) resins and for the articles produced therefrom.

13 Claims, No Drawings

TIN SALTS OF DIMERCAPTOETHYL FORMAL, RELATED COMPOUNDS AND PVC RESINS STABILIZED THEREWITH

BACKGROUND OF THE INVENTION

This invention relates to the art of organo tin compounds, the art of stabilization of polymers, and the art of polythioethers and polythioformals. Poly(vinyl chloride) is relatively unstable to heat and light. Initiation by heat involves rupture of the carbon-chlorine bond adjacent to a structure such as terminal unsaturation which reduces its stability. Initiation by ultraviolet light which is absorbed at unsaturated structures also results in release of adjacent chlorine atoms. The chlorine radical formed by either initiating event then abstracts hydrogen to form HCl. The chain radical forms chain unsaturation with consequent generation of another chlorine radical. The presence of oxygen accelerates the process and serves to introduce ketonic structures in the chain.

Improvement in the heat and light stability requires the addition of stabilizers. Metallic salts of tin, lead, barium or cadmium are used. Oxides, hydroxides, or fatty acid salts have been commonly considered among the most effective. Dialkyl tin mercaptides particularly those derived from mercapto-acetic and mercaptopropionic esters are known among this group of stablizers.

The present invention provides novel dialkyl or diaryl tin mercapto derivatives which are suitable for use as stabilizers for poly(vinyl chloride).

Applicant is unaware of any art materially relevant to the invention of this application.

SUMMARY OF THE INVENTION

The invention provides in a composition aspect a compound of the formula (I):

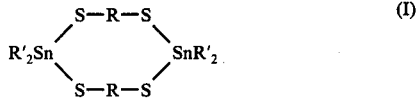

Wherein R is $-(CH_2)_m-(OCH_2)_p-O+(CH_2)_m-(OCH_2)_p+_n(CH_2)_m-$

Wherein $p$ is 0 or 1, $m$ is 2 to about 6, and $n$ is 0 to about 6; and R' is lower alkyl of up to about 10 carbon atoms, or carbocyclic aryl containing 1 or 2 aromatic rings.

The tangible embodiments of this composition aspect of the invention possess the inherent physical properties of being mobile liquids of low volatility, being substantially insoluble in water and soluble in such common organic solvent as toluene and acetone.

The nature of the starting materials, the mode of synthesis and the resemblance to analogous known materials further confirms the structure assigned the compounds sought to be patented.

The tangible embodiments of this composition aspect of the invention possess the inherent applied use characteristic of being ultraviolet light stabilizers for poly(vinyl chloride).

The invention provides in another composition aspect a light and heat stabilized composition based on poly(vinyl chloride) which comprises:

(a) a poly(vinyl chloride) resin; and
(b) a compound of Formula I.

The invention also provides in a process aspect a process for the preparation of a heat and light stabilized composition based on a poly(vinyl chloride) resin which comprises: blending with a poly(vinyl chloride) resin an effective amount of a compound of Formula I.

Special mention is made of the composition and process aspects of the invention wherein in the tangible embodiments of Formula I $p$ is 1, $m$ is 2, $n$ is 0 and R' is n-butyl.

DESCRIPTION OF THE PREFERRED EMBODIMENTS

The manner of making and using the compositions of the invention will now be described with reference to a specific embodiment thereof namely; a typical general purpose poly(vinyl chloride) resin, Geon 103 (supplied by B. F. Goodrich Co.) containing 7,7,17,17-tetrabutyl -1,3,11,13-tetraoxa -6,8,16,18-tetrathia -7,17-di-stannacycloeicosane (Ia).

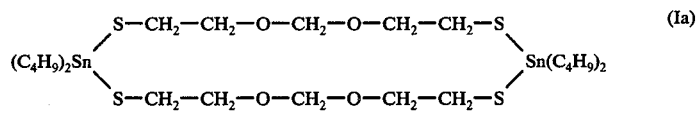

To prepare this composition the Geon 103, if desired, a plasticizer, conveniently dioctyl phthalate and Ia may be compounded together either on hot rolls or in a hot mixer such as Banbury. Upon cooling the composition, if plasticized, may then be calendered into sheets, films, or floor covering, or it may be extruded for such uses as wire insulation or tubing and hosing. If unplasticized, the compositions may be used in molding applications such as the production of phonograph records.

It will be obvious to one skilled in the art that in place of the Geon 103 poly(vinyl chloride) resin described, any of the commercially available poly(vinyl chloride) resins may be substituted in the aforesaid process to obtain analogous products therefrom. Similarly, if it is desired to employ a plasticizer, other conventional plasticizers such as trioctylphosphate, dioctyl sebacate and adipate and various low molecular weight polymers such as poly(propylene gylcol) esters or even tricresyl phosphate, dibutyl phthalate, dibutyl sebacate, or tributyl phosphate or mixtures thereof may be used in place of or together with dioctylphthalate illustrated. The optimum concentration of such plasticizer will of course vary according to the desired end use, but it will be the amount normally used for such application and it will be readily selected by one skilled in the art. Typically plasticizer may be added up to about 50% of the total composition weight, with about 30% being usual for film and sheeting applications. It will also be obvious that it place of the compound Ia illustrated, one may substitute any of the other compounds contemplated under Formula I to prepare equivalent stabilized compositions.

Ia may be prepared by treating bis (β-chloro-ethyl) formal (II) with sodium hydrosulfide in aqueous solution under hydrogen sulfide gas pressure at ambient temperatures to produce a compound of the formula:

HSCH$_2$CH$_2$OCH$_2$O(CH$_2$CH$_2$SCH$_2$CH$_2$OCH$_2$O)$_n$CH$_2$CH$_2$SH  (III)

wherein n may vary from 0 to about 6 depending on the relative concentrations of II, NaHS and the H$_2$S pressure. A higher concentration of NaHS and increased H$_2$S pressure results in lower values of n. If desired III wherein n is 0 (IIIa) may be distilled from the originally prepared III which one skilled in the art will readily appreciate to contain a mixture of n values. Similarly fractions of III having greater n values may be obtained from the originally prepared mixture by standard separation techniques, for example, molecular sieve chromatography. IIIa may be treated with dibutyl tin oxide in an inert solvent, conveniently n-butanol or toluene, at moderately elevated temperatures, conveniently about 80° to 120° C., preferably about 110° to 115° C., until evolution of water formed during the reaction ceases. If desired, Ia so formed may be recovered from the reaction mixture by standard techniques.

It will be obvious to one skilled in the art that bis (ω-chloro-alkyl) formals and bis (ω-chloro-alkyl) ethers may also be reacted with sodium hydrosulfide and hydrogen sulfide in similar fashion to that illustrated hereinabove, that the products so formed may be separated into their relative molecular sizes or mixtures thereof by standard techniques as described hereinabove and that these products may be reacted with known dialkyl or diaryl tin oxides to produce the other compounds contemplated under Formula I. Similarly II may be reacted with other known dialkyl or diaryl tin oxides to produce still other compounds of Formula I.

The compounds of the invention also possess pesticidal activity and they may be employed in standard formulations well known in the art for that purpose. Ia, for example, may be employed at concentrations up to 3% as an antibarnacle additive in standard marine paint formulations.

The following examples further illustrate the best mode contemplated by the inventor for the practice of his invention.

EXAMPLE 1

Dimercaptoethyl Formal

Bis (β-chloroethyl)formal (173 g.) in water (1000 ml.) is stirred with NaHS (320 g.) under H$_2$S (20 psi.) for 48 hours. At the end of this period, the layers are separated and the organic phase washed several times with water and dried to give a crude product (150 g.). Distillation gives the title product (BPt. 80° C., 0.5 mm. of Hg absolute pressure).

Analysis for C$_5$H$_{12}$O$_2$S$_2$
Calc: S, 38.2%
Found: S, 37%

EXAMPLE 2

7,7,17,17-tetrabutyl -1,3,11,13-tetraoxa -6,8,16,18-tetrathia -7,17-Distannacycloeicosane Bis (β-thioethyl) formal (100.3 g.) is stirred in toluene (150 g.) with dibutyltin oxide (114.2 g.) at about 85° to 115° C. while collecting the water evolved over a 40 minute period. At the end of this period water evolution ceased and refluxing is continued at about 115° C. for an additional 2 hours and the mixture cooled to room temperature. The solvent is removed in vacuo. The residue is taken up in methyl ethyl ketone and filtered through filter paper and the filtrate evaporated in vacuo to give the title product as an oil (180.2 g.)

Analysis for C$_{26}$H$_{56}$O$_4$S$_4$Sn$_2$ Found: C, 39.86; H, 7.54; S, 17.51; Sn, 0.36%

EXAMPLE 3

Formulations are prepared by hot mixing Geon 103 (100 parts by weight) and dioctyl phthalate (20 parts by weight) (A) and Geon 103 (100 parts by weight), dioctyl phthalate (20 parts by weight) and the product of example 2 (0.5 parts by weight) (B).

Initially A had a chocolate brown color and B had a very light yellow color. At the end of 1 day exposure to broad spectrum UV light A had a dark brown coloration tending to black while B maintained its light yellow color. At the end of 2 weeks, A had attained a jet black color while B was brown tinged black.

The subject matter which applicant regards as his invention is particularly pointed out and distinctly claimed as follows:

1. A compound of the formula:

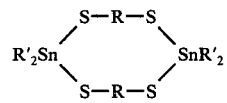

wherein R is $-(CH_2)_m-(OCH_2)_p-O-[(CH_2)_m-(OCH_2)_p-O]_n-(CH_2)_m-$ wherein p is 0 to 1, m is 2 to about 6 and n is 0 to about 6; and R' is lower alkyl of up to about 10 carbon atoms, or carbocyclic aryl containing 1 or 2 aromatic rings.

2. A compound as defined in claim 1 wherein p is 1.
3. A compound as defined in claim 1 wherein m is 2.
4. A compound as defined in claim 2 wherein m is 2.
5. A compound as defined in claim 1 wherein n is 0.
6. A compound as defined in claim 2 wherein n is 0.
7. A compound as defined in claim 3 wherein n is 0.
8. A compound as defined in claim 4 wherein n is 0.
9. A compound as defined in claim 1 wherein R' is lower alkyl.
10. A compound as defined in claim 1 wherein R' is n-butyl.
11. A compound as defined in claim 8 wherein R' is n-butyl.
12. A light and heat stabilized composition based on poly(vinyl chloride) which comprises:
   (a) a poly(vinyl chloride) resin; and
   (b) a compound of the formula:

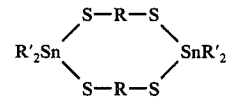

wherein R and R' are as defined in claim 1.

13. A process for the preparation of a heat and light stabilized composition based on a poly(vinyl chloride) resin which comprises blending with a poly(vinyl chloride) resin an effective amount of a compound of the formula:

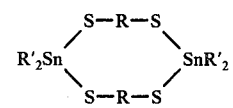

wherein R and R' are as defined in claim 1.